United States Patent [19]

Zaromb

[11] Patent Number: 4,829,008
[45] Date of Patent: May 9, 1989

[54] ANALYTICAL INSTRUMENT WITH APPARATUS FOR SAMPLE CONCENTRATING

[75] Inventor: Solomon Zaromb, Hinsdale, Ill.

[73] Assignee: The United States of America as represented by the United States Department of Energy, Washington, D.C.

[21] Appl. No.: 892,990

[22] Filed: Aug. 4, 1986

[51] Int. Cl.$^4$ .............................................. G01N 1/18
[52] U.S. Cl. .................... 436/178; 436/161; 436/168; 422/69; 422/70; 55/16; 55/158; 73/61.1 C; 73/863.23
[58] Field of Search ................... 436/178, 168, 161; 422/69, 70, 52, 53; 55/16, 158; 73/61.1 C, 863.23

[56] References Cited

U.S. PATENT DOCUMENTS

| 3,352,644 | 11/1967 | Lysyj | 436/178 X |
| 3,751,879 | 8/1973 | Allington | 55/158 |
| 4,311,789 | 1/1982 | Nylen et al. | 436/178 X |
| 4,529,521 | 7/1985 | Cortes et al. | 436/161 X |

FOREIGN PATENT DOCUMENTS 130994 10/1979 Japan .................................. 436/178

OTHER PUBLICATIONS

"Sampling and Determiniation of Gas-Phase Hydrogen Peroxide Following Removal of Ozone by Gas-Phase Reaction with Nitric Oxide", vol. 58, No. 8 of Analytical Chemistry, pp. 1857–1865 (Jul. 1986) by Tanner et al.
Article entitled "Silicone Rubber Tubing for Elimination of Background Conductivity in Anion Chromatography", Analytical Chemistry, 1984, vol. 56, p. 1033, Siemer et al.
"Carbon Dioxide Permeable Tubing for Postsuppression in Ion Chromatography", by Darryl D. Siemer, American Chemical Society, 1984.

Primary Examiner—Barry S. Richman
Assistant Examiner—Lynn M. Kummert
Attorney, Agent, or Firm—Hugh W. Glenn; Robert J. Fisher; William R. Moser

[57] ABSTRACT

A system for analysis of trace concentrations of contaminants in air includes a portable liquid chromatograph and a preconcentrator for the contaminants to be analyzed. The preconcentrator includes a sample bag having an inlet valve and an outlet valve for collecting an air sample. When the sample is collected the sample bag is connected in series with a sorbing apparatus in a recirculation loop. The sorbing apparatus has an inner gas-permeable container containing a sorbent material and an outer gas-impermeable container. The sample is circulated through the outer container and around the inner container for trapping and preconcentrating the contaminants in the sorbent material. The sorbent material may be a liquid having the same composition as the mobile phase of the chromatograph for direct injection thereinto. Alternatively, the sorbent material may be a porous, solid body, to which mobile phase liquid is added after preconcentration of the contaminants for dissolving the contaminants, the liquid solution then being withdrawn for injection into the chromatograph.

14 Claims, 3 Drawing Sheets

ANALYTICAL INSTRUMENT WITH APPARATUS FOR SAMPLE CONCENTRATING

CONTRACTUAL ORIGIN OF THE INVENTION

The United States government has rights in this invention pursuant to Contract No. W-31-109-ENG-38 between the U.S. Department of Energy and the University of Chicago, representing Argonne National Laboratory.

BACKGROUND OF THE INVENTION

The present invention relates to analytical instruments for detecting hazardous materials, and in particular to portable instruments.

This invention relates to analytical devices and, more specifically, to devices for detecting and analyzing trace concentrations of contaminants in a gaseous medium, such as air. A portable analytical system and method combining chromatography and an array of electrochemical sensors is disclosed in the copending U.S. application of Solomon Zaromb and Joseph R. Stetter, Ser. No. 881,310, filed July 2, 1986, entitled "Portable System and Method Combining Chromatography and Array of Electrochemical Sensors and assigned to the assignee of the present invention, the disclosure of which application is incorporated herein by reference. While a variant of that system, comprising a liquid chromatograph, has provided effective identification and concentration measurement of several hazardous contaminants in liquid samples, it has been found that the detection of very low or trace concentrations of these contaminants in air samples by that system requires a high degree of preconcentration into a small volume of liquid.

The use of absorbents, such as charcoal or Tenax for preconcentrating in gas chromatogrphy has several objectionable features, including the necessity for time-consuming and somewhat complicated desorption and sorbent-reconditioning steps and possible introduction of interfering contaminants from the sorbents. The use of cryogenic methods of preconcentration have been attempted, but are seriously limited by the necessity to use a sample volume of only about 10 cc to achieve 100% collection efficiency. The use of such a small sample volume means that the lower detection limit for contaminants of interest is about 1 ppb (part per billion) in air. It would be desirable to have about 100 times lower detection limits for certain contaminants of interest, e.g. the highly mutagenic two-and three-ring primary aromatic amines, such as the anthracyl-amines.

SUMMARY OF THE INVENTION

It is a general object of the invention to provide an improved analytical system which avoids the disadvantages of prior systems, while affording additional structural and operating advantages.

An important feature of the invention is the provision of an analytical system that is portable, and is yet capable of efficiently analyzing contaminants that may be encountered in air in trace concentrations.

In connection with the foregoing feature, it is another feature of the invention to provide a system of the type set forth which utilizes liquid chromatography.

In connection with the foregoing features, yet another feature of the invention is the provision of a system of the type set forth, wherein an air sample containing the trace contaminants is preconcentrated, the sample volume being sufficient to provide lower detection limits, at least as low as 0.01 ppb of the contaminant.

It is another feature of the invention to provide a system of the type set forth which is of relatively simple and economical construction.

Another feature of the invention is the provision of a preconcentrating apparatus for use in an analytical system of the type set forth.

These and other features of the invention are attained by providing apparatus for preconcentrating traces of contaminants in a gaseous medium for subsequent analysis by chromatography, said apparatus comprising: sorbing means having a gas-impermeable outer container and a gas-permeable inner container containing contaminant-sorbing material, means for circulating a sample of the gaseous medium through said outer container and around said inner container of said sorbing means for trapping and preconcentrating the traces of contaminants in said sorbing material, and means for removing said preconcentrated traces of contaminants from said sorbing means in a fluid sample for injection into an associated chromatograph.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

BRIEF DESCRIPTION OF THE DRAWINGS

For the purpose of facilitating an understanding of the invention, there is illustrated in the accompanying drawings a preferred embodiment thereof, from an inspection of which, when considered in connection with the following description, the invention, its construction and operation, and many of its advantages should be readily understood and appreciated.

DESCRIPTION OF THE PREFERRED EMBODIMENTS

Figure 1:
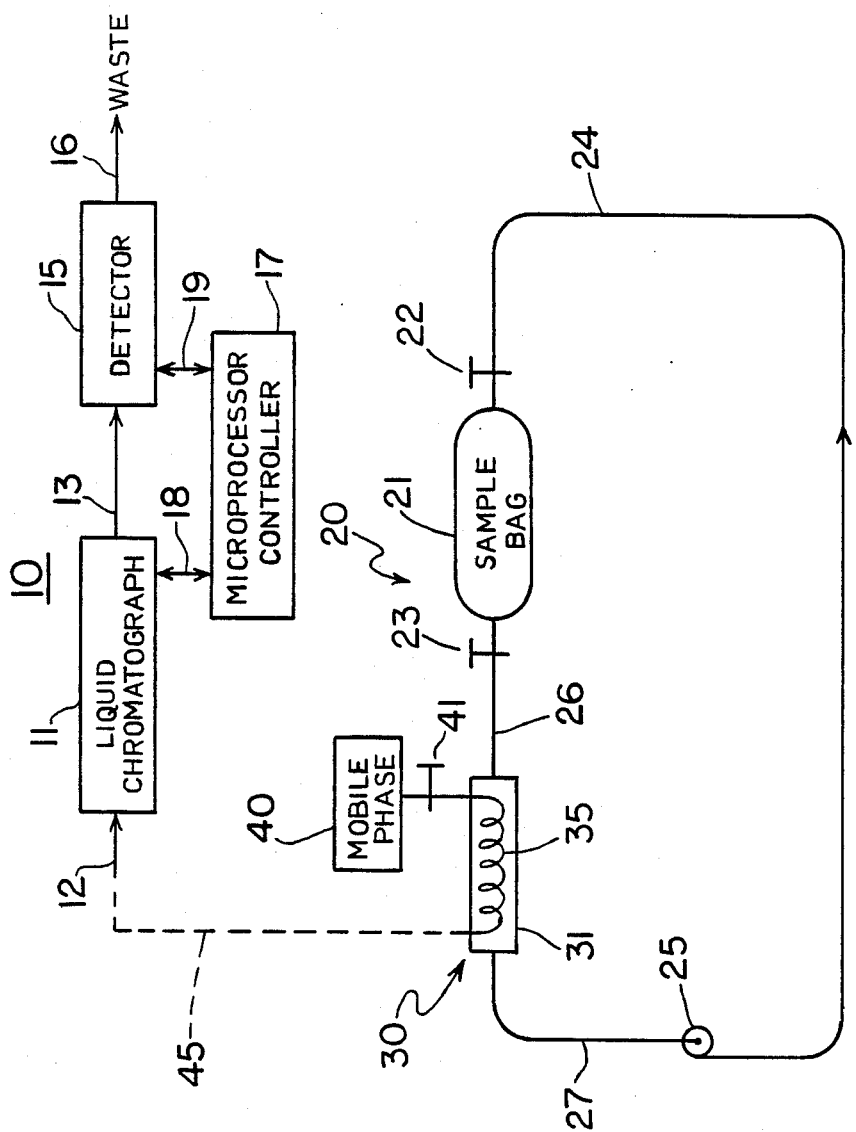
FIG. 1 is a block diagram illustrating an analytical system constructed in accordance with and embodying the features of the present invention.

Referring to FIG. 1, there is illustrated an analytical system, generally designated by the numeral 10, constructed in accordance with and embodying the features of the present invention. The system 10 includes a liquid chromatograph 11 having a sample inlet 12 and an outlet 13 which is coupled to the inlet of a CPS (chemical parameter spectrometer) or alternative detector having a waste outlet conduit 16. The liquid chromatograph 11 and the detector 15 are coupled to a microprocessor controller 17 by cables 18 and 19, respectively. Preferably, the liquid chromatograph 11, the detector 15 and the microprocessor controller 17 cooperate to form a portable analytical instrument of the type disclosed in the aforementioned copending application Ser. No.

881,310. More particularly, the detector 15 preferably comprises an array of sensors, in combination with a conditioning means for controlling operational conditions of the sensors. The microprocessor controller 17 operates under stored program control for controlling the operation of the liquid chromatograph 11 and the detector 15, and for identifying and determining the concentrations of contaminants being analyzed. Suitable display means (not shown) may be provided for use with the microprocessor controller 17 to display the results of the analysis.

The analytical system 10 also includes a sample preconcentrator 20 for preconcentrating trace quantities of the contaminants of interest in air. The preconcentrator 20 includes a sample bag 21 having an inlet valve 22 and an outlet valve 23. In use, the inlet valve 22 is adapted to be coupled to one end of a conduit 24, the other end of which is coupled to the outlet port of a pump 25. The outlet valve 23 of the sample bag 21 is adapted to be coupled, in use, to one end of a conduit 26, the other end of which is coupled to the inlet of a sorbing device 30. The outlet of the sorbing device 30 is coupled to one end of a conduit 27, the other end of which is coupled to the inlet port of the pump 25.

Figure 2:
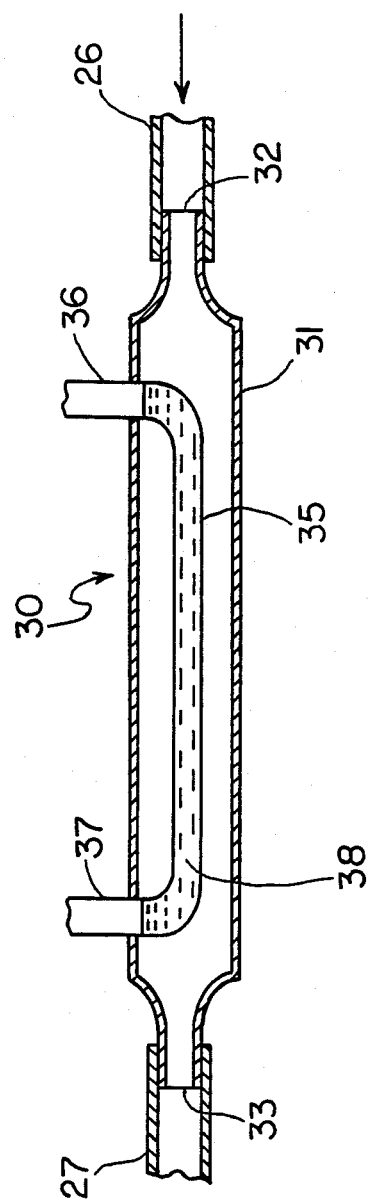
FIG. 2 is an enlarged, fragmentary view in vertical section of a sample preconcentrator in accordance with a first embodiment of the present invention for use in the system of FIG. 1.

Referring also to FIG. 2, the sorbing device 30 is a permeation absorber, including an elongated, tubular outer container 31, formed of a suitable fluid-impermeable material, and having tapered, reduced-diameter ends, respectively forming an inlet nipple 32 and an outlet nipple 33, dimensioned to be respectively fitted in the adjacent ends of the conduits 26 and 27. Disposed within the outer container 31 is an elongated tubular inner container 35, formed of a suitable gas-permeable material. The opposite ends of the inner container 35 terminate in fluid-impermeable inlet and outlet nipples 36 and 37, which respectively extend through complementary openings in the outer container 31. The inner container 35 may be either straight, as illustrated in FIG. 2, or coiled, as indicated in FIG. 1. The inner container 35 is substantially filled with a suitable contaminant-absorbing liquid sorbent 38.

The sorbing device 30 also includes a source, such as a reservoir 40, of liquid preferably having a composition substantially the same as that of the mobile phase of the liquid chromatograph 11, so that it may be used as such mobile phase. When the sorbing device 30 is of the type illustrated in FIG. 2, the liquid in the reservoir 40 is the contaminant-absorbing liquid sorbent 38. The reservoir 40 is coupled through a suitable valve 41 to the inlet nipple 36 of the inner container 35. The outlet nipple 37 of the inner container 35 may be coupled through an outlet conduit 45 to the inlet 12 of the liquid chromatograph 10. Alternatively, the liquid sorbent 38 may be withdrawn from the inner container 35 manually with a syringe through the outlet nipple 37 and then injected into the inlet 12 of the liquid chromatograph 11.

The outer container 31 of the sorbing device 30 preferably has an inner diameter of about 1 cm and is formed of a nonadsorbing material, such as glass, polyethylene or a polytetrafluoroethylene material, such as that sold by DuPont de Nemours and Co., Inc. under the trademark "TEFLON". The inner container 35 may be made of a suitable porous, gas-permeable material with hydrophobic pores, such as a porous polytetrafluoroethylene, of the type sold by W. L. Gore & Associates, Inc. under the trademark "GORE-TEX". The inner container 35 preferably has an inner diameter of about 1.0 mm with a 0.4 mm wall thickness, 3.5 micron maximum pore size and 70% porosity. The liquid sorbent 38 cannot pass through the hydrophobic pores in the inner container 35, and, for the absorption of primary aromatic amines, may consist of 35% tetrahydrofuran/65% $H_2O$ by volume at pH 2.2 (with a phosphate buffer). The volume of liquid required to fill the inner container 35 is about 0.12 cc, which is just about the right size fluid sample for use in analysis by the liquid chromatograph 11.

The sample bag 21 is preferably made of an inert material having minimum adsorptivity for the contaminants of interest. Usually, polytetrafluoroethylene is the material most suitable for sample bags. The sample bag 21 is covered with an opaque material to minimize light-induced reactions of the contaminants with air. Preferably the sample bag 21 has a volume of between 1 and 5 L.

In operation, to obtain an air sample, the inlet and outlet valves 22 and 23 of the sample bag 21 are disconnected from the conduits 24 and 26, and one of the valves 22 and 23 is closed. The other valve, which remains open, is connected first to the suction end of a suitable air pump (not shown) until the bag 21 is fully collapsed, i.e., completely empty. The open valve is then connected to a sampling pump (not shown) and filled with an air sample at a fixed flow rate for a fixed length of time (e.g., 2 L/min. for 2 min. to give a 4-L sample volume). The open valve is then closed tight to prevent loss of sample. The sample bag 21 is reconnected to conduits 24 and 26, the valves 22 and 23 are fully opened, and the pump 25 is turned on. The air sample in the sample bag 21 is thus circulated through the sorbing device 30 and the sample bag 21 at a rate and for a length of time sufficient to make several complete passes through the system (e.g., 5 min. at a rate of 1 L/min. for a 1-L sample, amounting to 5 passes). During this circulation, the air sample passes through the outer container 31 of the sorbing device 30 and around the inner container 35 in contact therewith. The trace contaminants in the air sample pass through the wall of the air-permeable inner container 35 of the sorbing device 30 and are trapped and preconcentrated in the liquid sorbent 38.

After the appropriate sample circulation time, the liquid sorbent 38 forms a preconcentrated fluid sample (of the contaminant of interest), which is either withdrawn manually with a syringe through the outlet nipple 37 and injected into the inlet 12 of the liquid chromatograph 11, or automatically withdrawn and transferred through the outlet conduit 45, which may be provided with suitable valving (not shown). The analysis of the fluid sample is then effected by the system 10, preferably in the same manner as described in the aforementioned copending application Ser. No. 881,310.

When the fluid sample has been withdrawn from the sorbing device 30, the inlet valve 22 of the sample bag 21 is disconnected from the conduit 24 and connected to a "zero air" filter, which removes most air contaminants, and the pump 25 is then caused to run for several minutes full speed so as to flush contaminant-free air through the sample preconcentrator 20 and remove most of the contaminants from the previous sample that may have been adsorbed onto the inner walls of the conduits 24, 26 and 27, the pump 25 and the sample bag 21. Finally, the inner container 35 is flushed with pure mobile phase liquid from the reservoir 40 by opening the valve 41 to remove any contaminant absorbed in the liquid remaining from the previous preconcentration step. The inner container 35 is then filled with a fresh supply of liquid sorbent 38 from the reservoir 40. The system is now ready for refilling the sample bag 21 with a fresh air sample to repeat the preconcentration procedure for the next fluid sample.

Figure 3:
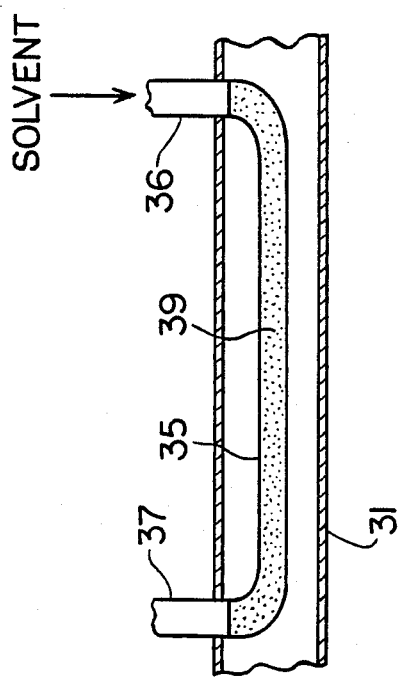
FIG. 3 is a fragmentary view, similar to FIG. 2, of an alternative embodiment of the sample preconcentrator of the present invention.

Referring to FIG. 3, there is illustrated an alternative embodiment of the sorbing device 30, wherein the inner container 35 is filled with a sorbent plug or body 39 of highly porous, high-surface-area, solid adsorbent material that would preferentially adsorb any contaminants present in the circulating air sample. In this embodiment of the invention, at the end of the air-circulation step, the sorbent body 39 can be filled with liquid mobile phase from the reservoir 40, the mobile phase being selected in this embodiment to preferentially dissolve the contaminant of interest from the sorbent body 39. The liquid solvent, with the contaminants dissolved therein, may then be withdrawn in a liquid sample and injected into the liquid chromatograph 11 in the manner described above.

When the embodiment of FIG. 3 is used, the inner container 35 could be made several times longer than that in the embodiment of FIG. 2, for the same volume of fluid sample, which may result in a much larger porous area through which the air contaminants may permeate and, therefore, in a faster rate of permeation of the contaminant of interest through the wall of the inner container 35. For instance, if the sorbent body 39 fills 80% of the inside volume of the inner container 35, then this container may be lengthened by a factor of 5 for the same volume of liquid sample as was provided in the embodiment of FIG. 2. This may reduce the number of passes of the air sample through the sorbing device 30 needed for satisfactory collection efficiency, thereby reducing the required air circulation time. However, this time saving may be offset by the additional time required to dissolve the contaminant from the sorbent body 39 into the mobile phase solvent and, thereafter, to recondition the sorbent body 39 for the next preconcentration step. Moreover, if any of the contaminant of interest tends to remain adsorbed at the pore walls of the inner container 35, then the increased pore area could adversely affect the lower detection limit for that contaminant.

When the analytical system 10 is used with the embodiments of either FIG. 2 or FIG. 3, care must be taken to prevent air leaks, and to have all the components of the system 10 that are in contact with the air sample made of inert and not highly adsorbent material, such as glass, polyethylene or polytetrafluoroethylene of the type sold under the trademark "TEFLON". When these conditions are met, it is estimated that collection efficiencies of 60–100% are obtainable for concentrations as low as 0.01 ppb of contaminants, such as primary aromatic amines.

From the foregoing, it can be seen that there has been provided an improved analytical system utilizing liquid chromatography and an effective sample preconcentrator, provided in a portable instrument of relatively simple and economical construction capable of efficiently detecting trace concentrations of contaminants in air.

The embodiments of the invention in which an exclusive property or privilege is claimed are defined as follows:

1. Apparatus for preconcentrating traces of analytes in a gaseous medium, said apparatus comprising: sorbing means having a gas-impermeable outer container and a gas-permeable inner container, analyte-sorbing material contained in said inner container, means for circulating a sample of gaseous medium through said outer container and around said inner container of said sorbing means for trapping and preconcentrating traces of analytes in said sorbing material, and means for removing said preconcentrated traces of analytes from said sorbing means in a fluid sample.

2. The apparatus of claim 1, wherein said analyte-sorbing material is a liquid sorbent.

3. The apparatus of claim 2, and further comprising an analytical instrument for receiving a fluid sample, said analytical instrument including a liquid chromatograph having a liquid mobile phase, said liquid sorbent having substantially the same composition as the mobile phase of the chromatograph.

4. The apparatus of claim 1, wherein said analyte-sorbing material is a solid sorbent.

5. The apparatus of claim 4, and further comprising a liquid chromatograph for receiving a fluid sample, said chromatograph having a liquid mobile phase, said removing means including means for adding to said sorbent material a liquid solvent for dissolving the preconcentrated traces of analytes, and means for withdrawing the liquid solvent with the analytes dissolved therein from said inner container.

6. The apparatus of claim 1, and further comprising a sample vessel, means for collecting a sample of gaseous medium in said sample vessel, said circulating means including means for circulating the sample of gaseous medium sequentially through said sorbing means and said sample vessel.

7. The apparatus of claim 6, wherein said sample vessel includes a sample bag having an inlet valve and an outlet valve.

8. A system for analyzing traces of analytes in a gaseous medium comprising: a portable apparatus having an inlet and an outlet for achieving analyses of components of a fluid sample, sorbing means having a gas-impermeable outer container and a gas-permeable inner container, analyte-sorbing material contained in said inner container, means for circulating a sample of gaseous medium through said outer container and around said inner container of said sorbing means for trapping and preconcentrating traces of analytes in said sorbing material, means for removing said preconcentrated traces of analytes from said sorbing means in a fluid sample, and means for injecting the fluid sample into said inlet of said apparatus.

9. The system of claim 8, and further comprising a sample vessel, means for collecting a sample of gaseous medium in said sample vessel, said circulating means including means for circulating the sample of gaseous medium collected sequentially through said sorbing means and through said sample vessel.

10. The system of claim 8, wherein said apparatus includes a liquid chromatograph having a liquid mobile phase.

11. The system of claim 10, wherein said analyte-sorbing material is a liquid sorbent.

12. The system of claim 10, wherein said analyte-sorbing material is a porous, solid sorbent body, said removing means including means for adding to said sorbent body a liquid solvent having a composition substantially the same as that of said mobile phase for dissolving said preconcentrated traces of analytes, and means for withdrawing said liquid solvent with the preconcentrated traces of analytes dissolved therein from said inner container.

13. The system of claim 10, and further comprising portable detection means communicating with said outlet for identifying and estimating the concentration of the components eluting therefrom.

14. The system of claim 13, and further comprising control means coupled to said liquid chromatograph and to said detection means for controlling the operations thereof.

* * * * *